(12) United States Patent
Ohkubo

(10) Patent No.: US 7,544,162 B2
(45) Date of Patent: Jun. 9, 2009

(54) OPTICAL PROBE

(75) Inventor: Kazunobu Ohkubo, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 307 days.

(21) Appl. No.: 11/529,533

(22) Filed: Sep. 29, 2006

(65) Prior Publication Data

US 2007/0076429 A1    Apr. 5, 2007

(30) Foreign Application Priority Data

Sep. 30, 2005  (JP)  ............................ 2005-288659
Feb. 17, 2006  (JP)  ............................ 2006-040621

(51) Int. Cl.
  *A61B 1/06*  (2006.01)
  *G02B 6/06*  (2006.01)
(52) U.S. Cl. ................ 600/173; 600/170; 385/117
(58) Field of Classification Search ................ 385/117, 385/118, 119; 600/137, 170, 173
  See application file for complete search history.

(56) References Cited

U.S. PATENT DOCUMENTS

| | | | |
|---|---|---|---|
| 3,804,081 A * | 4/1974 | Kinoshita et al. | ........... 600/167 |
| 6,546,272 B1 | 4/2003 | MacKinnon et al. | |
| 6,564,087 B1 | 5/2003 | Pitris et al. | |
| 2004/0076390 A1 * | 4/2004 | Dong Yang et al. | ......... 385/116 |
| 2004/0254474 A1 | 12/2004 | Seibel et al. | |
| 2005/0177026 A1 | 8/2005 | Hoeg et al. | |

FOREIGN PATENT DOCUMENTS

| | | |
|---|---|---|
| JP | 6-165784 A | 6/1994 |
| JP | 2002-005822 A | 1/2002 |
| JP | 2003-139688 A | 5/2003 |
| WO | WO 02/088684 A1 | 11/2002 |

* cited by examiner

*Primary Examiner*—Alessandro Amari
(74) *Attorney, Agent, or Firm*—Sughrue Mion, PLLC

(57) ABSTRACT

An optical probe has a tubular outer envelope, and a shaft rotatable about a rotating axis extending longitudinal direction of the outer envelope. A light guide disposed to extend along the shaft is connected to the shaft at its leading end portion, a light deflector connected to the leading end portion of the light guide deflects light radiated from the leading end portion of the light guide, and a collecting lens converges light radiated from the light deflector outside the outer envelope. Light emitted from the light deflector is scanned along the outer envelope in response to movement of the shaft and the light deflector is connected to the shaft in a position deviated from the axis of rotation of the shaft and is movable to the shaft so that the direction of light deflected by the light deflector can be changed in this position.

2 Claims, 12 Drawing Sheets

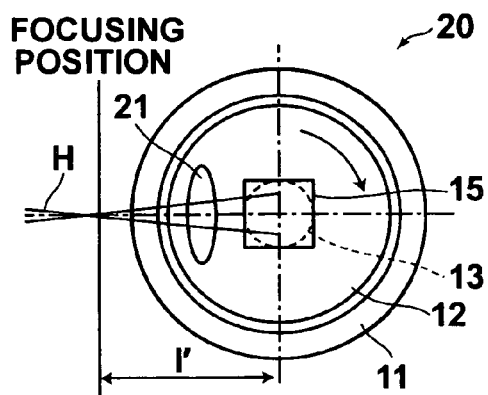
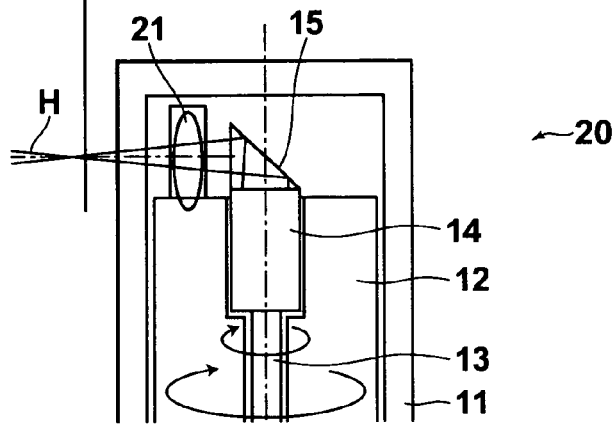
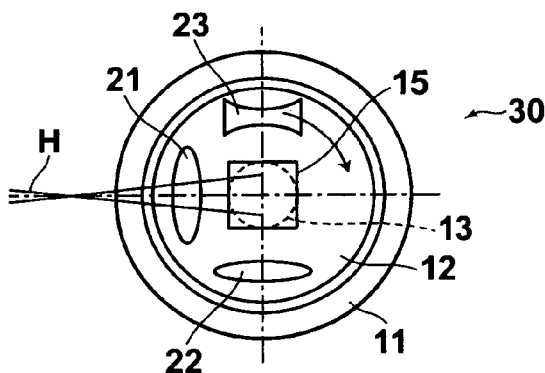
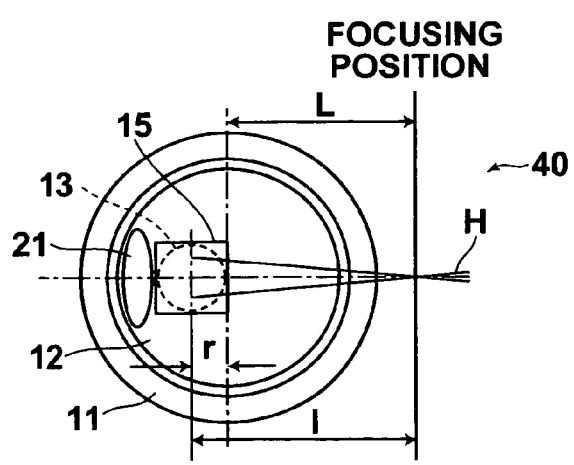

FOCUSING POSITION

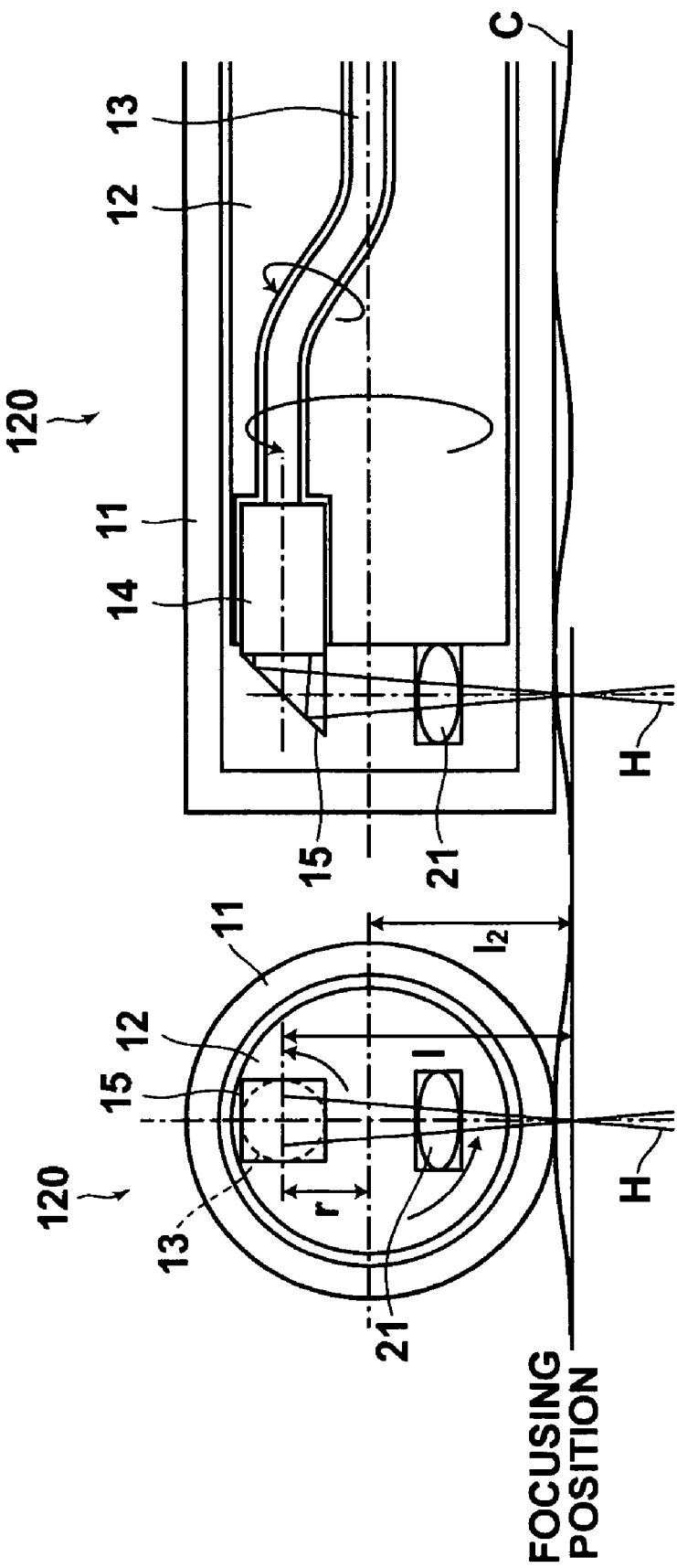

OPTICAL PROBE

BACKGROUND OF THE INVENTION

1. Field of the Invention

This invention relates to an optical probe, and more particularly to an optical probe having a tubular outer envelope and having a function of deflecting and scanning light emitted from the peripheral surface thereof in the direction of circumference or the axis of the outer envelope.

2. Description of the Related Art

As a method of obtaining a tomographic image of an object of measurement such as living tissue, it is proposed to obtain a tomographic image of the object by measuring OCT (optical coherence tomography) as disclosed in Japanese Unexamined Patent Publication Nos. 6(1994)-165784 and 2003-139688. In the OCT measurement, a phenomenon that interference light is detected when the optical paths of the measuring light and the reflected light conform to the optical path of the reference light in length is used. That is, in this method, low coherent light emitted from a light source is divided into measuring light and reference light and the measuring light is projected onto the object of measurement, while the reflected light from the object of measurement is led to a multiplexing means. The reference light is led to the multiplexing means after its optical path length is changed in order to change the depth of measurement in the object. By the multiplexing means, the reflected light and the reference light are superposed one on another, and interference light due to the superposition is detected by, for instance, heterodyne detection.

In the above OCT system, a tomographic image is obtained by changing the optical path length of the reference light, thereby changing the measuring position (the depth of measurement) in the object. This technique is generally referred to as "TD-OCT (time domain OCT)". More specifically, in the optical path length changing mechanism for the reference light disclosed in Japanese Unexamined Patent Publication No. 6(1994)-165784, an optical system which collects the reference light emitted from the optical fiber on a mirror is provided and the optical path length is adjusted by moving only the mirror in the direction of the beam axis of the reference light. Further, in the optical path length changing mechanism for the reference light disclosed in Japanese Unexamined Patent Publication No. 2003-139688, the reference light emitted from the optical fiber is turned to parallel light, the reference light in the form of parallel light is collected and caused to enter the optical fiber again by an optical path length adjusting lens, and the optical path length adjusting lens is moved back and forth in the direction of the beam axis of the reference light.

Whereas, as a system for rapidly obtaining a tomographic image without changing the optical path length of the reference light, there has been proposed an optical tomography system for obtaining an optical tomographic image by measurement of SD-OCT (spectral domain OCT). In the SD-OCT system, a tomographic image is formed without scanning in the direction of depth, by dividing broad band, low coherent light into measuring light and reference light by the use of a Michelson interferometer, projecting the measuring light onto the object and carrying out a Fourier analysis on each channeled spectrum obtained by decomposing the interference light of the reflected light, which returns at that time, and the reference light.

As another system for rapidly obtaining a tomographic image without changing the optical path length of the reference light, there has been proposed an optical tomography system for obtaining an optical tomographic image by measurement of SS-OCT (swept source OCT). In the SS-OCT system, the frequency of the laser beam emitted from the light source is swept to cause the reflected light and the reference light to interfere with each other at each wavelength, the intensity of the reflected light at the depth of the object is detected by Fourier-transforming the spectrum of the interference for the series of wavelength, and a tomographic image is formed by the use of the intensity of the reflected light at the depth of the object.

In the optical tomography system of each of the systems described above, a tomographic image along a certain surface of the object is generally obtained and for this purpose, it is necessary to at least one-dimensionally scan the measuring light beam in the object. As a means for effecting such a light scanning, there has been known, as disclosed in Japanese Unexamined Patent Publication No. 2002-005822 and International Patent Publication No. WO02/088684, an optical probe having a tubular outer envelope and having a function of deflecting and scanning light emitted from the peripheral surface thereof in the direction of circumference of the outer envelope. More specifically, the optical probe comprises a tubular outer envelope (sheath) closed at the leading end thereof, a shaft which is rotatable about an axis of rotation extending longitudinal direction of the outer envelope inside the outer envelope, a light guide means such as an optical fiber which is disposed inside the outer probe to extend along the shaft and is connected to the shaft at its leading end portion, a light deflecting means which is connected to the leading end portion of the light guide means and deflects light radiated from the leading end portion of the light guide means in a direction intersecting the axis of rotation of the shaft, and a collecting lens which converges light radiated from the light deflecting means outside the outer envelope, and deflects and scans light emitted from the light deflecting means in the direction of circumference of the outer envelope.

Further, as an optical probe similar to that described above, there has been known an optical probe which comprises a light guide means, a and a collecting lens similar to those described above in addition to a tubular outer envelope and a shaft movable in the longitudinal direction of the outer envelope inside the outer envelope, and causes light radiated from the light deflecting means to scan linearly in the direction of the movement in response to movement of the shaft in the longitudinal direction of the outer envelope.

When an optical tomographic image is to be obtained by the use of the optical probe described above, there has been a requirement that the focusing position (converging position) of the light beam which scans the object is changed according to the depth of the part to be observed. Further, there has been a requirement that the NA of the light beam which scans the object is changed according to the region to be observed and/or the resolution to be desired.

In the optical probe disclosed in Japanese Unexamined Patent Publication No. 2002-005822, the thickness of the outer envelope (sheath) is locally varied so that the position of the focusing position of the light beam can be changed.

However, in the above structure, though the focusing position is varied according to the eccentric position of the housing when the sheath is mounted thereon, how to control the eccentric position of the housing is not established yet. That is, though, when the focusing position happens to be conformed when the sheath is mounted on the housing, the focusing position of the light beam will satisfy, the focusing position cannot be changed when it is deviated from the intended position. Even if the focusing position can be changed by externally rotating the sheath, the field of view is shifted in response to rotation of the sheath, which makes it impossible to view both a shallower part and a deeper part in the same field of view.

On the other hand, in the optical probe disclosed in International Patent Publication No. WO02/088684, the lens on the leading end portion of the probe is moved in the direction of the optical axis by the wire or the hydraulic pressure to change the distance between the light outlet end of the optical fiber and the lens, thereby changing the magnification (NA, depth of focus) of the lens or to change the distance between the lens and the reflecting mirror, thereby changing the focusing position.

However, in the above structure, since the wire or the hydraulic pipe must be passed through the probe, the space inside the probe is increased, and at the same time, it is necessary to make provision against interference of the fiber and the sheath. Further, since the magnification of the lens and the focusing position are driven by separate drive systems (including wire or hydraulic pressure), a pair of drive systems must be prepared to simultaneously drive the magnification of the lens and the focusing position. To pass a pair of drive systems through a probe to separately drive is more difficult to pass a single drive system through the probe and there is a fear that the drive systems can interfere with each other. Further, when the focal point adjusting system is to be driven to correct the deviation in focusing position generated when the magnification of the lens is changed, the two drive systems must be interlocked. For this purpose, a highly sophisticated control mechanism is required, which adds to the cost. Further, when the drive system is driven to shift the position of the optical fiber in the direction of the axis, the position of the optical fiber is shifted with respect to the optical fiber from the tomography system body. When the optical fiber on the probe side is coupled to the optical fiber on the body side through a direct coupling (ends of the optical fibers are directly mated), the distance between two fibers becomes too large to obtain an excellent coupling unless a mechanism which moves the body side fiber according to the movement of the probe side fiber. Though the change in position can be dealt with insertion of a confocal optical system, this approach requires additional lenses and increases the cost.

SUMMARY OF THE INVENTION

In view of the foregoing observations and description, the primary object of the present invention is to provide an optical probe which is simple in mechanism and can freely change the NA and/or the focusing point of the light beam to be rotatively or linearly scanned.

In accordance with the present invention, there is provided a first optical probe comprising a tubular outer envelope, a shaft which is rotatable about an axis of rotation extending longitudinal direction of the outer envelope inside the outer envelope, a light guide means which is disposed inside the outer probe to extend along the shaft and is connected to the shaft at least at its leading end portion, a light deflecting means which is connected to the leading end portion of the light guide means and deflects light radiated from the leading end portion of the light guide means, and a collecting lens which converges light radiated from the light deflecting means outside the outer envelope, wherein the improvement comprises that light emitted from the light deflecting means is rotatively scanned in the direction of circumference of the outer envelope in response to rotation of the shaft and the light deflecting means is connected to the shaft in a position deviated from the axis of rotation of the shaft and is movable relatively to the shaft so that the direction of light deflected by the light deflecting means can be changed in this position.

In accordance with the present invention, there is further provided a second optical probe comprising a tubular outer envelope, a shaft which is rotatable about an axis of rotation extending longitudinal direction of the outer envelope inside the outer envelope, a light guide means which is disposed inside the outer probe to extend along the shaft and is connected to the shaft at least at its leading end portion, a light deflecting means which is connected to the leading end portion of the light guide means and deflects light radiated from the leading end portion of the light guide means, and a collecting lens which converges light radiated from the light deflecting means outside the outer envelope, wherein the improvement comprises that light emitted from the light deflecting means is rotatively scanned in the direction of circumference of the outer envelope in response to rotation of the shaft and at least one NA changing lens is mounted on the shaft while the light deflecting means is movable relatively to the shaft so that a state where light radiated therefrom is passed through the NA changing lens and a state where light radiated therefrom is not passed through the NA changing lens can be set.

In accordance with the present invention, there is further provided a third optical probe comprising a tubular outer envelope, a shaft which is movable in the longitudinal direction of the outer envelope inside the outer envelope, a light guide means which is disposed inside the outer probe to extend along the shaft and is connected to the shaft at its leading end portion, a light deflecting means which is connected to the leading end portion of the light guide means and deflects light radiated from the leading end portion of the light guide means, and a collecting lens which converges light radiated from the light deflecting means, wherein the improvement comprises that light emitted from the light deflecting means is linearly scanned in the direction of movement of the shaft in response to movement of the shaft in the longitudinal direction of the outer envelope and the light deflecting means is connected to the shaft in a position deviated from the central axis of the shaft to be movable relatively to the shaft so that the direction of light deflected by the light deflecting means can be changed in this position and is rotatable about an axis parallel to the longitudinal direction of the outer envelope inside the outer envelope.

In accordance with the present invention, there is further provided a fourth optical probe comprising a tubular outer envelope, a shaft which is movable in the longitudinal direction of the outer envelope inside the outer envelope, a light guide means which is disposed inside the outer probe to extend along the shaft and is connected to the shaft at least at its leading end portion, a light deflecting means which is connected to the leading end portion of the light guide means and deflects light radiated from the leading end portion of the light guide means, and a collecting lens which converges light radiated from the light deflecting means, wherein the improvement comprises that light emitted from the light deflecting means is linearly scanned in the direction of movement of the shaft in response to movement of the shaft in the longitudinal direction of the outer envelope and at least one NA changing lens is mounted on the shaft while the light deflecting means is movable relatively to the shaft so that a state where light radiated therefrom is passed through the NA changing lens and a state where light radiated therefrom is not passed through the NA changing lens can be set.

In the second and fourth optical probes of this embodiment, it is preferred that a plurality of the NA changing lenses are provided and the light deflecting means is movable relatively to the shaft so that the NA changing lens which light radiated from the light deflecting means is passed through can be selected.

The second optical probe may be structured to change the direction of light deflection (the direction in which light radiated from the leading end portion of the light guide means is deflected) in combination of the structure of the first optical probe.

Similarly, the fourth optical probe may be structured to change the direction of light deflection in combination of the structure of the third optical probe.

Further, in the optical probes of the present invention, it is preferred that an optical fiber be employed as the light guide means and the optical fiber connected to the shaft at its leading end portion be movable relatively to the shaft by rotation of the optical fiber about its axis.

The first optical probe of the present invention, since the light deflecting means is connected to the shaft in a position deviated from the axis of rotation of the shaft and is movable relatively to the shaft so that the direction of light deflected by the light deflecting means can be changed in this position, can freely change the distance between the focusing position of light by the collecting lens and the axis of rotation of the shaft, that is, the focusing position in the direction of depth of the object.

When the focusing position can be thus changed, the depth of taking an image can be freely changed when a tomographic image of the object is to be obtained. Since the focusing position can be changed by only moving the light deflecting means relatively to the shaft, the optical probe is simple in structure and can be manufactured at low cost.

In the second optical probe of the present invention, since at least one NA changing lens is mounted on the shaft and the light deflecting means is movable relatively to the shaft so that a state where light radiated therefrom is passed through the NA changing lens and a state where light radiated therefrom is not passed through the NA changing lens can be set, the NA of light to be projected onto the object can be changed at least in two ways. It is possible to also change the focusing position in response to setting a state where light radiated therefrom is passed through the NA changing lens and a state where light radiated therefrom is not passed through the NA changing lens. Further, it is possible to structure the second optical probe so that the focusing position is kept unchanged when the NA is changed by combining the structure of the second optical probe with the structure of the first optical probe.

When the NA of light can be thus changed, the lateral resolution (the dynamic range) can be changed when a tomographic image of the object is to be obtained. When also the focusing position can be changed together with the lateral resolution at that time, the depth of taking an image and the lateral resolution can be simultaneously changed. When the focusing position is kept unchanged in response to change of the NA, only the lateral resolution can be switched without changing the depth of taking an image.

Since the NA of light can be changed by only moving the light deflecting means relatively to the shaft, the second optical probe is simple in structure and can be manufactured at low cost.

In the third optical probe of the present invention, since the light deflecting means is connected to the shaft in a position deviated from the axis of rotation of the shaft and is movable relatively to the shaft so that the direction of light deflected by the light deflecting means can be changed in this position, the distance between the focusing position of light by the collecting lens and the axis of rotation of the shaft is changed in response to the relative movement of the light deflecting means.

However, when the direction of light deflection is changed by moving the light deflecting means relatively to the shaft, the direction of light radiation from the shaft is also changed. Since, in the third optical probe, unlike the first optical probe, light is not rotatively scanned by rotating the shaft, but is linearly scanned in the longitudinal direction of the outer envelope, it is necessary to make constant the direction of light radiation from the shaft (normally in the direction of depth of focus) in a cross-section normal to the direction, and/or to make constant the direction of joining the focusing position and the axis of the shaft upon a slant projection (a projection toward a direction having an angle to the direction of depth of focus). Accordingly, when the shaft rotatable inside the outer envelope about an axis parallel to the longitudinal direction of the outer envelope is rotated in this direction, these requirements can be satisfied.

By changing the distance between the focusing position of light and the central axis of the shaft while holding constant the direction of light radiation from the shaft in the manner described above, the focusing position in the direction of depth of the object can be freely changed.

In the fourth optical probe of the present invention, since at least one NA changing lens is mounted on the shaft and the light deflecting means is movable relatively to the shaft so that a state where light radiated therefrom is passed through the NA changing lens and a state where light radiated therefrom is not passed through the NA changing lens can be set as in the second optical probe, the NA of light to be projected onto the object can be changed at least in two ways. Further, in the fourth optical probe, it is possible to also change the focusing position in response to setting a state where light radiated therefrom is passed through the NA changing lens and a state where light radiated therefrom is not passed through the NA changing lens. Further, it is possible to structure the fourth optical probe so that the focusing position is kept unchanged when the NA is changed by combining the structure of the fourth optical probe with the structure of the second optical probe.

When the NA of light can be thus changed, the lateral resolution (the dynamic range) can be changed when a tomographic image of the object is to be obtained. When also the focusing position can be changed together with the lateral resolution at that time, the depth of taking an image and the lateral resolution can be simultaneously changed. When the focusing position is kept unchanged in response to change of the NA, only the lateral resolution can be switched without changing the depth of taking an image.

Since, in the fourth optical probe, the NA of light can be changed by only moving the light deflecting means relatively to the shaft, the fourth optical probe is simple in structure and can be manufactured at low cost.

BRIEF DESCRIPTION OF THE DRAWINGS

FIGS. 6A and 6B are respectively a plan cross-sectional view and a side cross-sectional view showing another state of the optical probe shown in FIGS. 5A and 5B, FIG. 7 is a plan cross-sectional view of an optical probe in accordance with a third embodiment of the present invention, FIG. 8 is a plan cross-sectional view of an optical probe in accordance with a fourth embodiment of the present invention, FIGS. 26A and 26B are respectively a front cross-sectional view and a side cross-sectional view showing another state of the optical probe shown in FIG. 25.

DESCRIPTION OF THE PREFERRED EMBODIMENTS

Figure 1A:
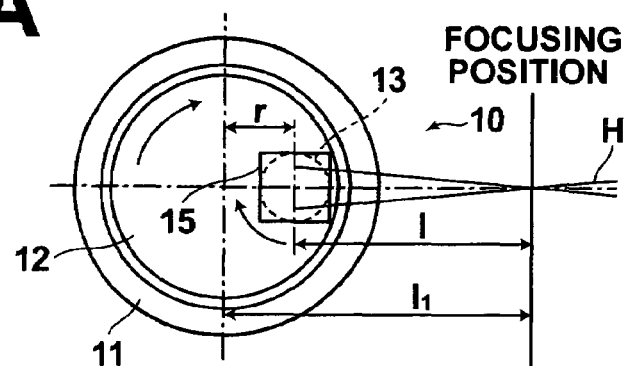
FIGS. 1A and 1B are respectively a plan cross-sectional view and a side cross-sectional view of an optical probe in accordance with a first embodiment of the present invention.
Figure 1B:
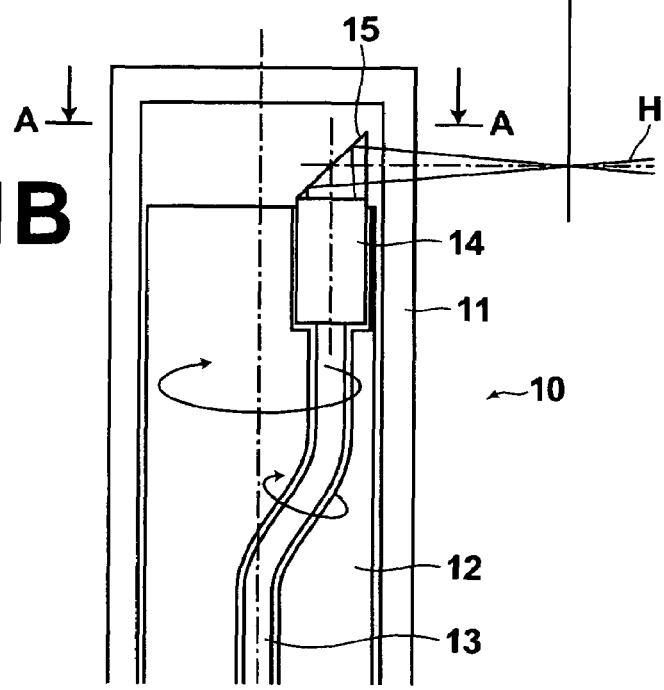

Embodiments of the present invention will be described in detail with reference to the drawings, hereinbelow. FIG. 1B shows a side cross-sectional shape of the leading end portion of an optical probe 10 in accordance with a first embodiment of the present invention and FIG. 1A is a plan cross-sectional view of the optical probe 10 taken along line A-A in FIG. 1B. For example, the optical probe 10 forms a leading end portion of an endoscope which forms a part of an optical tomography system.

The optical probe 10 comprises a cylindrical sheath 11 which is closed at its leading end and is formed by transparent material, and a flexible shaft 12 which is disposed inside the optical probe 10 for rotation about the axis of the sheath 11. An optical fiber 13 which guides light from an interferometer (not shown) is passed through the flexible shaft 12, and GRIN lens (refractive index profile lens) 14 and a reflecting mirror 15 are disposed in the leading end portion of the flexible shaft 12. The optical fiber 13, the GRIN lens 14 and the reflecting mirror 15 are integrated and a portion from the leading end of the optical fiber to the reflecting mirror 15 is disposed in a position deviated from the axis of rotation of the flexible shaft 12 by r and is rotatable inside the flexible shaft 12.

In the optical probe 10, light beam H propagated through the optical fiber 13 is collected by the GRIN lens 14 and changes its direction of travel at the reflecting mirror 15 by 90°, thereby being converged on an outer portion of the circumference of the sheath 11. When the flexible shaft 12 is rotated inside the sheath 11 by the driving means (not shown), the light beam H radiated outward of the circumference of the sheath 11 is deflected, whereby when the object is on the outer side of the sheath 11, the light beam H scans (rotatively scans) the object in the circumferential direction of the sheath 11.

When it is assumed in this structure that the distance from the reflecting mirror 15 to the focusing position of the GRIN lens 14 is 1, the distance $l_1$ from the axis of rotation of the flexible shaft 12 to the focusing position of the GRIN lens 14 is expressed by the following formula (1) in the setup shown in FIGS. 1A and 1B.

$$l_1 = l + r \quad (1)$$

Figure 2A:
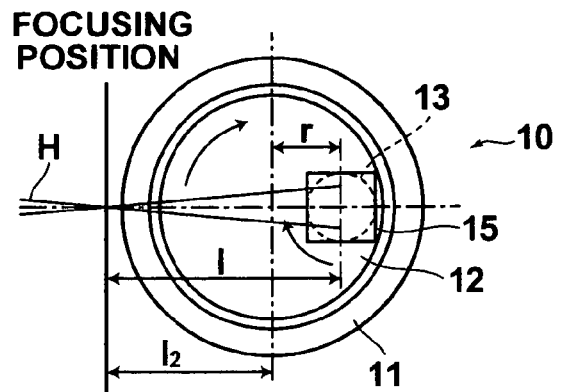
FIGS. 2A and 2B are respectively a plan cross-sectional view and a side cross-sectional view showing another state of the optical probe shown in FIGS. 1A and 1B.
Figure 2B:
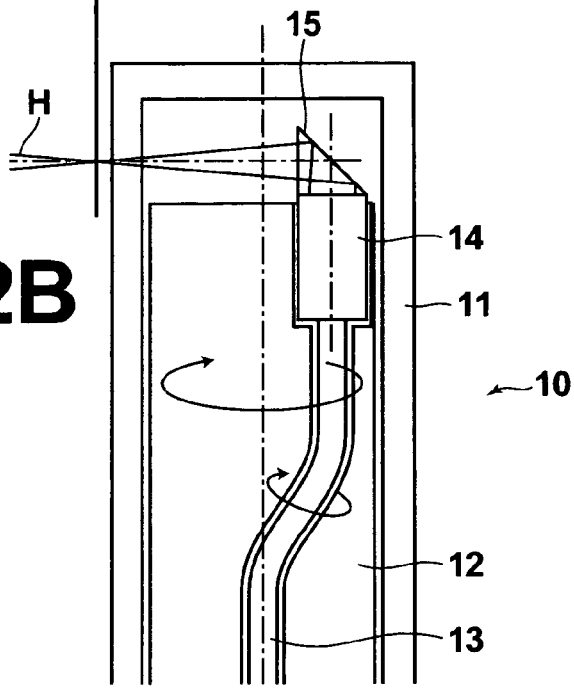

Whereas, FIGS. 2A and 2B show a state where the optical fiber 13 is rotated in the flexible shaft 12 to make the direction of light radiation of the reflecting mirror 15 reverse to that shown in FIGS. 1A and 1B. The distance from the axis of rotation of the flexible shaft 12 to the focusing position at this time is expressed by the following formula (2).

$$l_2 = l - r \quad (2)$$

That is, the distance from the center of the rotary scanning of the light beam H to the focusing position can be freely changed between the maximum $l_1$ and the minimum $l_2$. The width of the change is expressed by the following formula (3).

$$l_1 - l_2 = 2r \quad (3)$$

When the outer diameter of the sheath 11 is R, the depth of the focusing position from the outer periphery of the sheath is $l_1-R$ at the largest and $l_2-R$ at the smallest. This is the actual range of the depth of the focusing position in the object.

Figure 3:
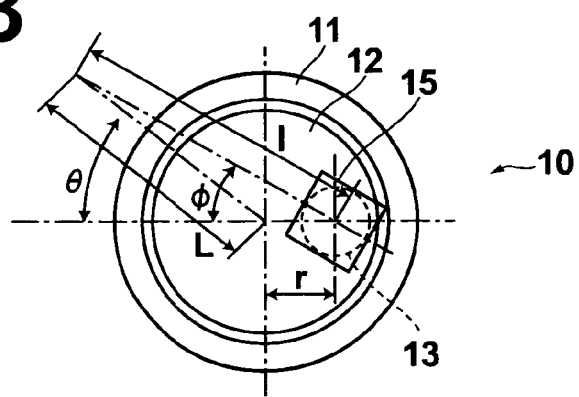
FIG. 3 is a plan cross-sectional view showing still another state of the optical probe shown in FIGS. 1A and 1B.

The case where the reflecting mirror 15 is inclined by a certain angle φ shown in FIG. 3 will be discussed next. When the distance from the reflecting mirror 15 to the focusing position is l, the distance L and the angle θ from the center of the rotary scanning of the light beam H to the focusing position are as expressed by the following formulae (4) and (5).

$$L=(l^2-2rl\cos\phi+r^2)^{1/2} \quad (4)$$

$$\theta=\tan^{-1}\{l\sin\phi/(l\cos\phi-r)\} \quad (5)$$

Since the distance L can be changed from $l_2$ to $l_1$ when the angle φ is changed from 0° to 180°, the focusing position can be continuously freely set.

Figure 4:
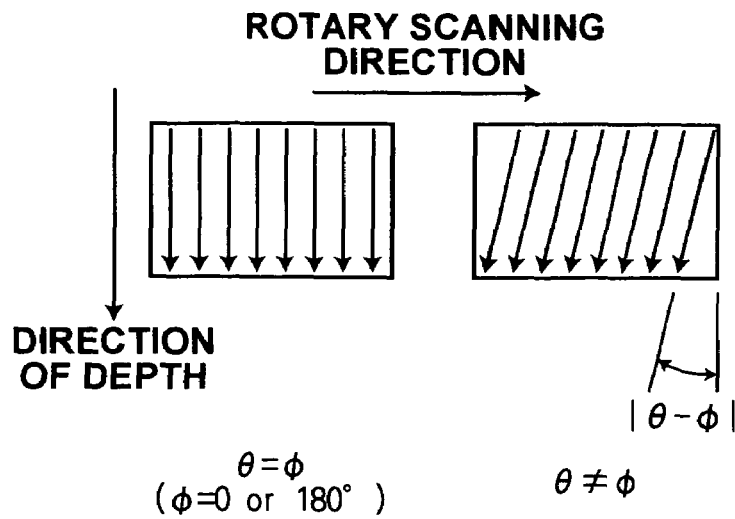
FIG. 4 is a view showing scanning of the optical probe shown in FIGS. 1A and 1B, FIGS. 5A and 5B are respectively a plan cross-sectional view and a side cross-sectional view of an optical probe in accordance with a second embodiment of the present invention.

However, it is necessary to take care that the obtained image is inclined by |θ−φ| since the direction of light projection in the direction of depth of the object is inclined by |θ−φ| with respect to a line extended to the focusing position from the axis of rotation of the flexible shaft 12. When a tomographic image is to be reconstructed, it is necessary to take into account the angular shift of the light scanning. FIG. 4 shows the inclination of the light scanning (rotary scanning).

Figure 19:
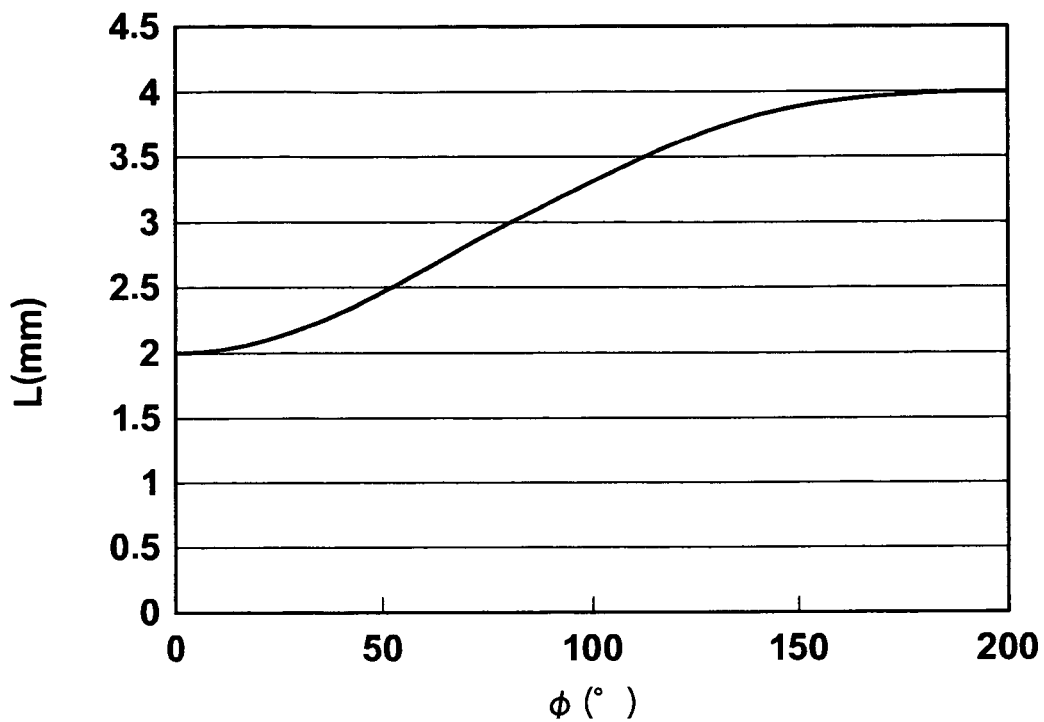
FIG. 19 is a graph showing the change of the distance L with the angle φ shown in FIG. 3.
Figure 20:
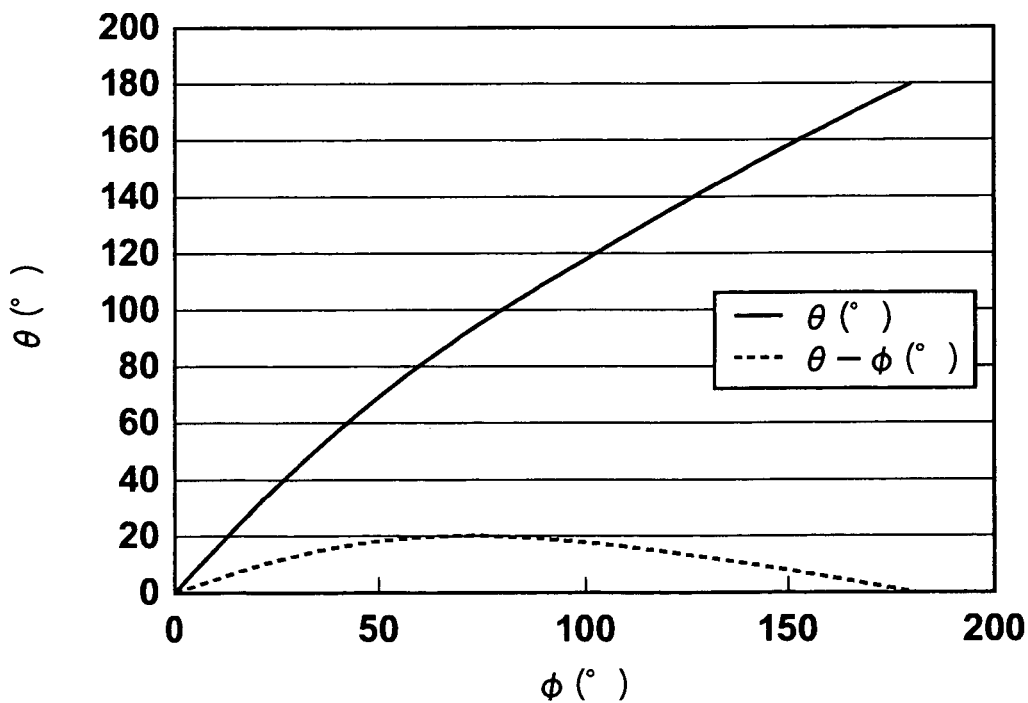
FIG. 20 is a graph showing the changes of the angle θ and the angle θ−φ with the angle φ shown in FIG. 3, FIGS. 21A and 21B are respectively a front cross-sectional view and a side cross-sectional view of an optical probe in accordance with a tenth embodiment of the present invention.

Further, FIG. 19 shows the change of the distance L with the angle φ when r=1 mm and l=3 mm, and FIG. 20 shows the changes of the angle θ−φ with the angle φ when r=1 mm and l=3 mm. When φ=0°, L=2 mm and when φ=180°, L=4 mm, and L can be continuously changed by changing φ from 0° to 180°. Further, since θ−φ is increased to about 20° at most, it will be found that the tilt angle of the scanning in the direction of depth of the object can be changed to 20° at most. Accordingly, it is necessary to carry out image processing taking into account the result.

Figure 5A:
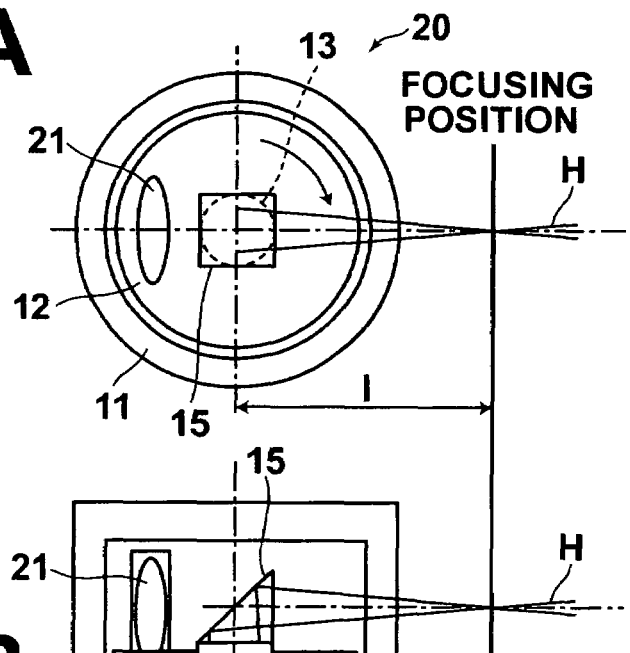
Figure 5B:
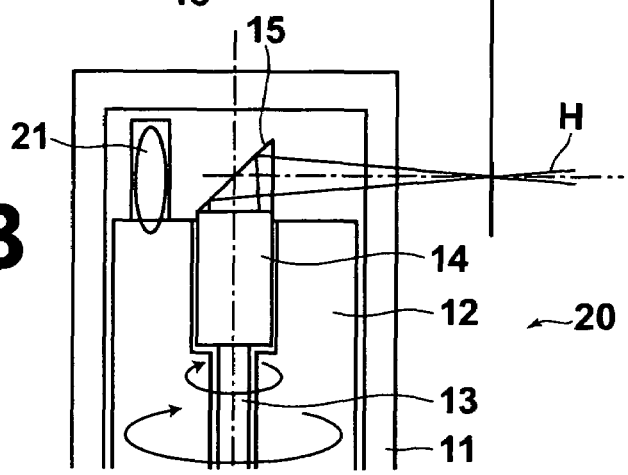

A second embodiment of the present invention will be described with reference to FIGS. 5A and 5B, hereinbelow. FIGS. 5A and 5B are respectively a plan cross-sectional view and a side cross-sectional view of an optical probe 20 in accordance with a second embodiment of the present invention. In FIGS. 5A and 5B, the elements analogous to those shown in FIGS. 1A and 1B are given the same reference numerals and will not be described unless necessary.

In the optical probe 20 of this second embodiment, the optical fiber 13 integrated with the GRIN lens 14 and the reflecting mirror 15 is disposed for rotation in the flexible shaft 12 coaxially therewith. A NA (aperture number) changing lens 21 is fixed to the leading end of the flexible shaft 12.

When the optical probe 20 is in the state shown in FIGS. 5A and 5B, light beam H radiated from the reflecting mirror 15 is projected onto the object without passing through the NA changing lens 21 and the distance from the reflecting mirror 15 to the focusing position is l.

When the optical fiber 13 is rotated to change the direction of the reflecting mirror 15 by 180° from that shown in FIGS. 5A and 5B, the state of the optical probe 20 shown in FIGS. 6A and 6B is obtained. In this state, light beam H radiated from the reflecting mirror 15 is projected onto the object after passing through the NA changing lens 21 and the distance from the reflecting mirror 15 to the focusing position is l'.

In the case where the NA changing lens 21 is a convex lens, the NA to the light beam H is increased from the case when the light beam H does not pass through the NA changing lens 21, and the lateral resolution in the focusing position is improved. Conversely, in the case where the NA changing lens 21 is a concave lens, the NA to the light beam H is decreased from the case when the light beam H does not pass through the NA changing lens 21, and the lateral resolution in the focusing position is deteriorated. As the NA increases, though being better in the focusing position, the lateral resolution is rapidly deteriorated when deviated from the focusing position in the direction of the optical axis (direction of depth of the object). By employing the arrangement of this embodiment, the NA can be reduced when the measurement is to be done over a range wide in the direction of depth, the NA can be increased when the measurement is to be done at a high resolution only at the aimed depth.

Though only one NA changing lens 21 is disposed on the leading end of the flexible shaft 12 in the second embodiment described above, a plurality of NA changing lenses 21, 22 and 23 different from each other in focal length are disposed on the leading end of the flexible shaft 12 in the third embodiment shown in FIG. 7. In this arrangement, when the lens which light beam radiated from the reflecting mirror 15 passes through is selected by adjusting the angular position of the optical fiber 13, the NA can be switched in a plurality of ways, whereby a more suitable resolution and a more suitable depth of focus can be set.

Figure 9:
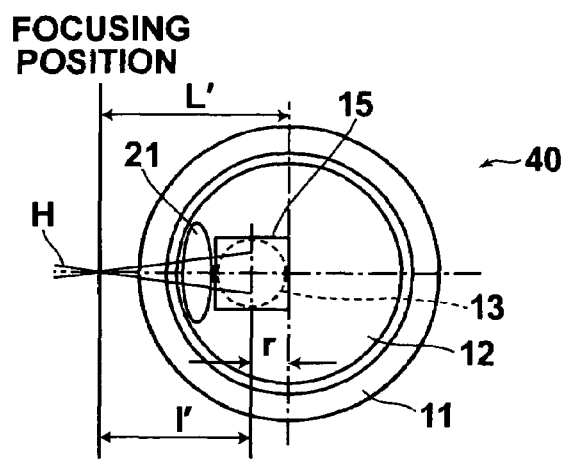
FIG. 9 is a plan cross-sectional view showing another state of the optical probe shown in FIG. 8.

A fourth embodiment of the present invention will be described with reference to FIGS. 8 and 9, hereinbelow. The optical probe 40 of the fourth embodiment is basically the same in structure as the first embodiment shown in FIGS. 1A, 1B, 2A and 2B and the NA changing lens 21 employed above in the second embodiment shown in FIGS. 5A and 5B is provided in addition.

When the optical probe 40 is in the state shown in FIG. 8, light beam H radiated from the reflecting mirror 15 is projected onto the object without passing through the NA changing lens 21 and the distance L from the center of the rotary scanning to the focusing position is L=l−r (6). In the state shown in FIG. 9, light beam H radiated from the reflecting mirror 15 is projected onto the object after passing through the NA changing lens 21 and the distance L' from the center of the rotary scanning to the focusing position is L'=l'+r (7).

When it is assumed that L=L', l−l'=2r (8) from formulae (6) and (7). When the magnification and the position of the NA changing lens 21 are determined so that the difference between the distance l between the reflecting mirror 15 and the focusing position when the NA changing lens 21 is provided and the distance l' between the reflecting mirror 15 and the focusing position when the NA changing lens 21 is not provided is equal to twice the diameter by which the optical fiber 13 is deviated from the center of rotation of the flexible shaft 12, the depth of measurement can be kept unchanged even after the NA is switched.

In the case of the second embodiment, though the resolution and the dynamic range in the direction of the depth can be switched by changing the NA, the focusing position is also changed simultaneously, whereby the field of view is jumped to another place which deteriorates convenience of use. Whereas, in the case of the fourth embodiment, the position in the direction of the depth can be kept unchanged even after the NA is switched. Accordingly, the field of view cannot be jumped and convenience of use can be improved.

Figure 10:
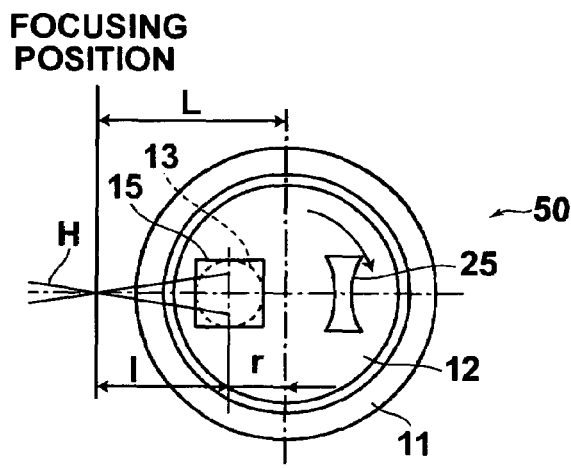
FIG. 10 is a plan cross-sectional view of an optical probe in accordance with a fifth embodiment of the present invention.
Figure 11:
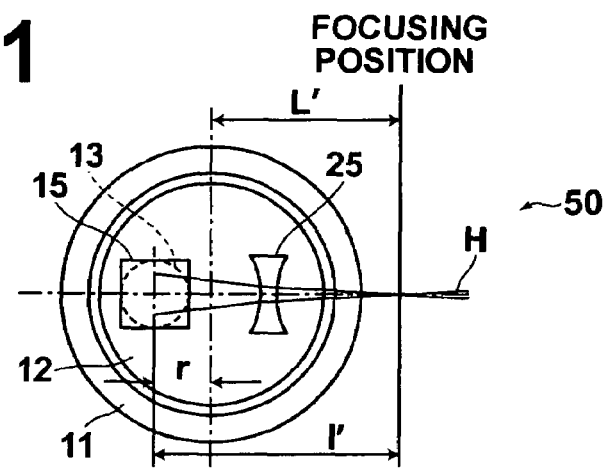
FIG. 11 is a plan cross-sectional view showing another state of the optical probe shown in FIG. 10, FIGS. 12A and 12B are respectively a side cross-sectional view of an optical probe in accordance with a sixth embodiment of the present invention, and a side cross-sectional view showing another state of the optical probe in accordance with the sixth embodiment of the present invention.

A fifth embodiment of the present invention will be described with reference to FIGS. 10 and 11, hereinbelow. In the optical probe 50 of the fifth embodiment, a concave lens is employed as the NA changing lens 25. In the fourth embodiment shown in FIGS. 8 and 9, limitation on design is lot when the probe is made thin since it is necessary to dispose the NA changing lens 21 on the same side as that in which the optical fiber is deviated from the center of rotation of the flexible shaft 12 to make L=L'. Whereas, when a concave NA changing lens 25 is employed as in this embodiment, freedom of design is increased and the probe can be made thin since the NA changing lens 25 is disposed on the side opposite to that in which the optical fiber is deviated from the center of rotation of the flexible shaft 12.

Figure 12A:
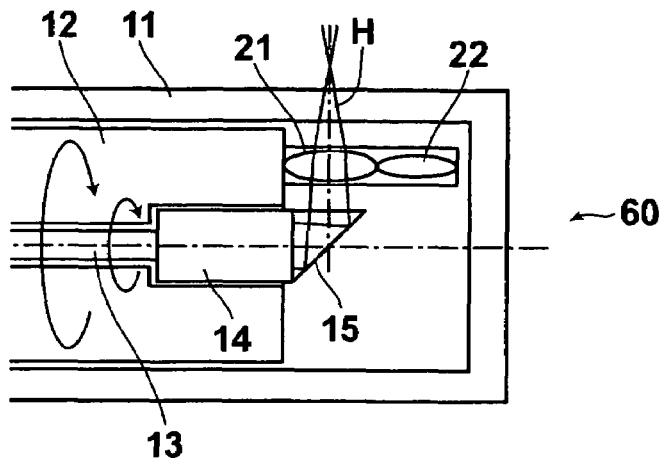
Figure 12B:
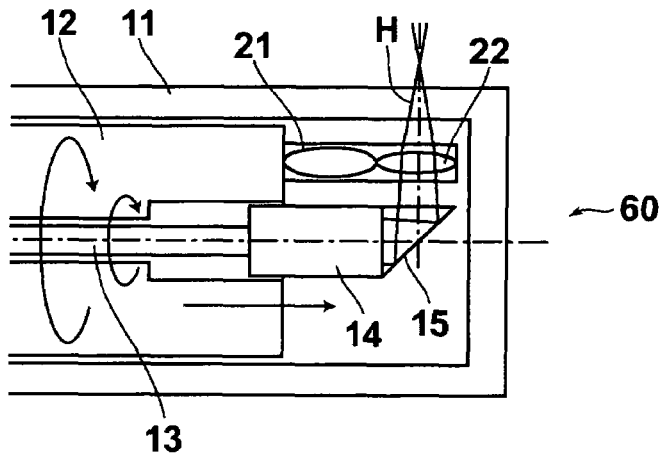

A sixth embodiment of the present invention will be described with reference to FIGS. 12A and 12B, hereinbelow. The optical probe 60 of the sixth embodiment is an improved type of the optical probe 20 of the second embodiment shown in FIGS. 5A and 5B. Though a plurality of NA changing lenses 21, 22 and 23 are fixed to the leading end of the flexible shaft 12 in arrangement in the circumference direction of the probe in the optical probe 30 of the third embodiment shown in FIG. 7, a plurality of (two by way of example) NA changing lenses 21 and 22 are fixed to the leading end of the flexible shaft 12 in arrangement in the longitudinal direction of the probe here.

A recess on the leading end of the flexible shaft 12 to accommodate the lenses is formed so that the GRIN lens 14 can be slide therein in the longitudinal direction of the probe. By moving the optical fiber 13 in the flexible shaft 12 in the direction of axis thereof, a state where the reflecting mirror 15 fixed to the GRIN lens 14 is opposed to one NA changing lenses 21 (FIG. 12A) and a state where the reflecting mirror 15 fixed to the GRIN lens 14 is opposed to the other NA changing lenses 22 (FIG. 12B) can be selected. In this embodiment, the NA of the light beam H is larger and the focusing position is outer in the former state.

As in the optical probe 20 in FIGS. 5A and 5B, when the optical fiber 13 is rotated to change the direction of the reflecting mirror 15 by 180°, a state where light beam H is passed through neither NA lens 21 nor NA lens 22 can be set.

When the arrangement of this embodiment is employed, three or more NA changing lenses may be disposed arranged in the longitudinal direction of the probe. Further, a plurality of NA changing lenses may be disposed arranged in the circumferential direction of the probe as shown in FIG. 7 in addition to a plurality of NA changing lenses arranged in the longitudinal direction of the probe so that the light beam H is led to one of a plurality of NA changing lenses arranged in the circumferential direction of the probe when the optical fiber 13 is rotated relatively to the flexible shaft 12. Further, it is possible to increase the number of options of the NA and/or the focusing position by combining such arrangement with the arrangement shown in FIGS. 1A and 1B, where the leading end portion of the optical fiber 13 is eccentric to the center of the flexible shaft 12.

Figure 13:
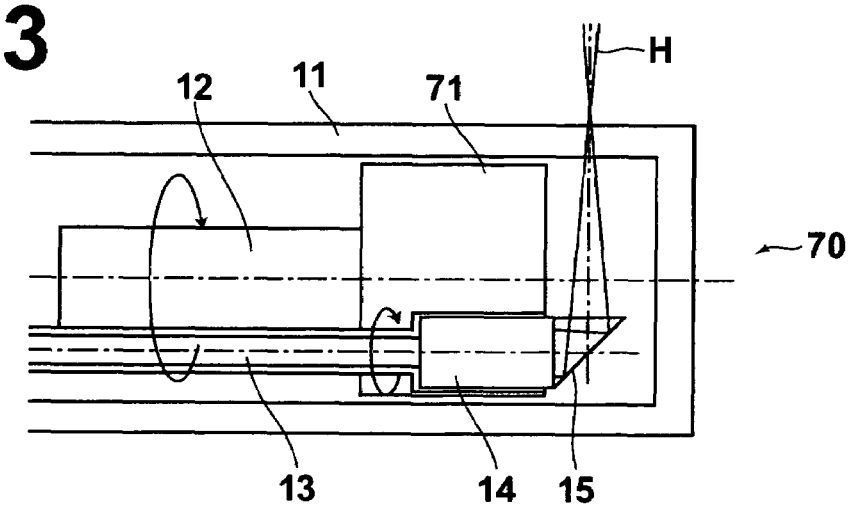
FIG. 13 is a side cross-sectional view of an optical probe in accordance with a seventh embodiment of the present invention.

A seventh embodiment of the present invention will be described with reference to FIG. 13, hereinbelow. In the optical probe 70 of the seventh embodiment, the flexible shaft 12 is sufficiently thinner as compared with the inner diameter of the sheath 11 and only a cylindrical head 71 fixed to the leading end is in sliding contact with the inner surface of the sheath 11.

In the first to sixth embodiments described above, the optical fiber 13 is passed in the flexible shaft 12, and accordingly, the outer diameter of the flexible shaft 12 is slightly smaller than the inner diameter of the sheath 11. However, if the flexible shaft 12 is thick, the sheath 11 and the flexible shaft 12 are brought into contact with each other when the probe is curved, and disturbance of the scanning, wear and/or generation of heat can be involved due to increase of the frictional resistance.

Whereas, the optical probe 70 of this embodiment, since the flexible shaft 12 is thin, is free from the problem described above. The cylindrical head 71 is larger than the flexible shaft 12 in the diameter and smaller than the inner diameter of the sheath 11 to such an extent that its axis cannot be shifted. By causing such a head 71 to hold the leading end portion of the optical fiber 13, the amount of eccentricity of the leading end portion of the optical fiber 13 from the center of the flexible shaft 12 can be held constant.

Figure 14:
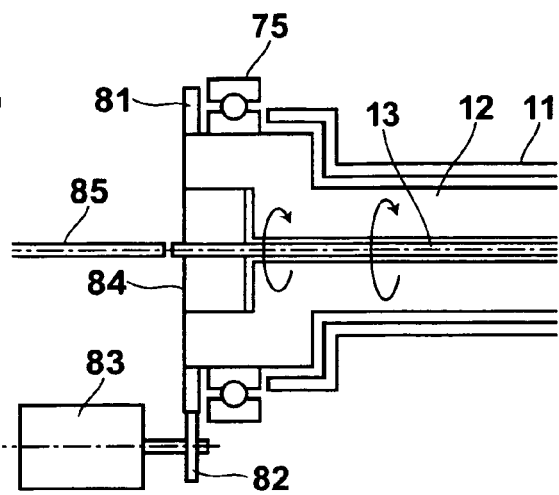
FIG. 14 is a side cross-sectional view showing the structure for connecting the optical probe of the present invention to the system body.

Connection of the optical probe and the tomography system body which can be applied to each of the embodiments described above will be described with reference to FIG. 14, hereinbelow. In this structure, the flexible shaft 12 is connected to the tomography system body by way of the shaft bearing 75 to be rotatable and to be rotated by a shaft rotating motor 83 by way of gears 81 and 82. A fiber rotating motor 84 is provided in the base of the flexible shaft 12 and is used to change the direction of the reflecting mirror 15 (e.g., FIGS. 1A and 1B) provided on the leading end portion of the optical fiber. A body side optical fiber 85 is fixed to the tomography system body and is connected to the rotary probe side optical fiber 13 by a direct coupling close thereto.

Figure 15:
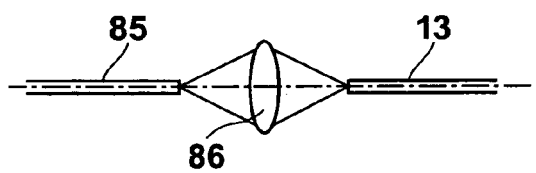
FIG. 15 is a side view showing an example of the structure for optically connecting the optical probe of the present invention to the system body.
Figure 16:
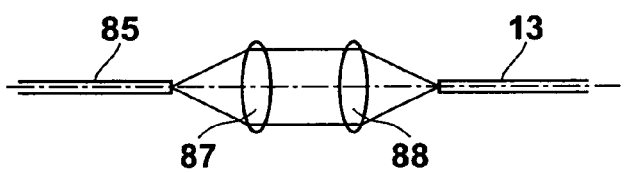
FIG. 16 is a side view showing another example of the structure for optically connecting the optical probe of the present invention to the system body.

The body side optical fiber 85 and the probe side optical fiber 13 may be connected by way of a lens system comprising a single lens 86 as shown in FIG. 15 or by way of a confocal optical system comprising a pair of lenses 87 and 88 as shown in FIG. 16 other than by the direct coupling described above.

Figure 17:
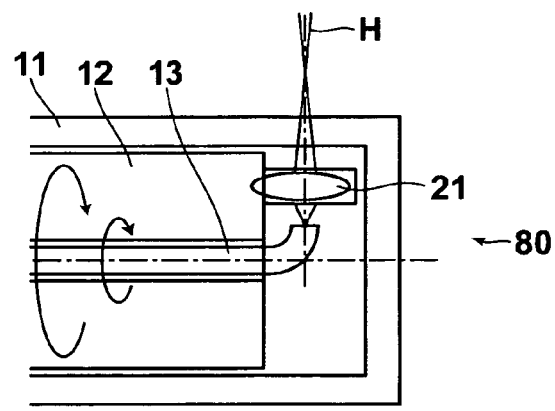
FIG. 17 is a side cross-sectional view of an optical probe in accordance with an eighth embodiment of the present invention.

An eighth embodiment of the present invention will be described with reference to FIG. 17, hereinbelow. Though a reflecting mirror 15 is employed as the light deflecting means in each of the embodiments described above, the leading end portion of the optical fiber 13 is bent to form the light deflecting means in this embodiment. With this arrangement, a state shown in FIG. 17 where light travels through the NA changing lens 21 and a state where light does not travel through the NA changing lens 21 (e.g., the leading end portion of the optical fiber 13 is directed downward in FIG. 17) can be set by changing the angular position of the optical fiber 13.

Figure 18:
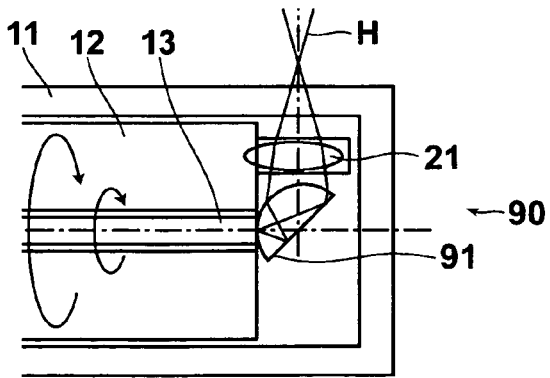
FIG. 18 is a side cross-sectional view of an optical probe in accordance with a ninth embodiment of the present invention.

A spherical lens 91 fixed to the leading end of the optical fiber 13 may be employed as the light deflecting means as in an optical probe 90 of a ninth embodiment shown in FIG. 18. Also with this arrangement, a state shown in FIG. 18 where light travels through the NA changing lens 21 and a state where light does not travel through the NA changing lens 21 (e.g., the surface of the spherical lens 91 having a curvature is directed downward in FIG. 18) can be set by changing the angular position of the optical fiber 13.

Though the optical probes in accordance with the embodiments of the present invention where light is rotatively scanned have been described above, the optical probes in accordance with the embodiments of the present invention where light is linearly scanned will be described, hereinbelow.

Figures 21A, 21B:
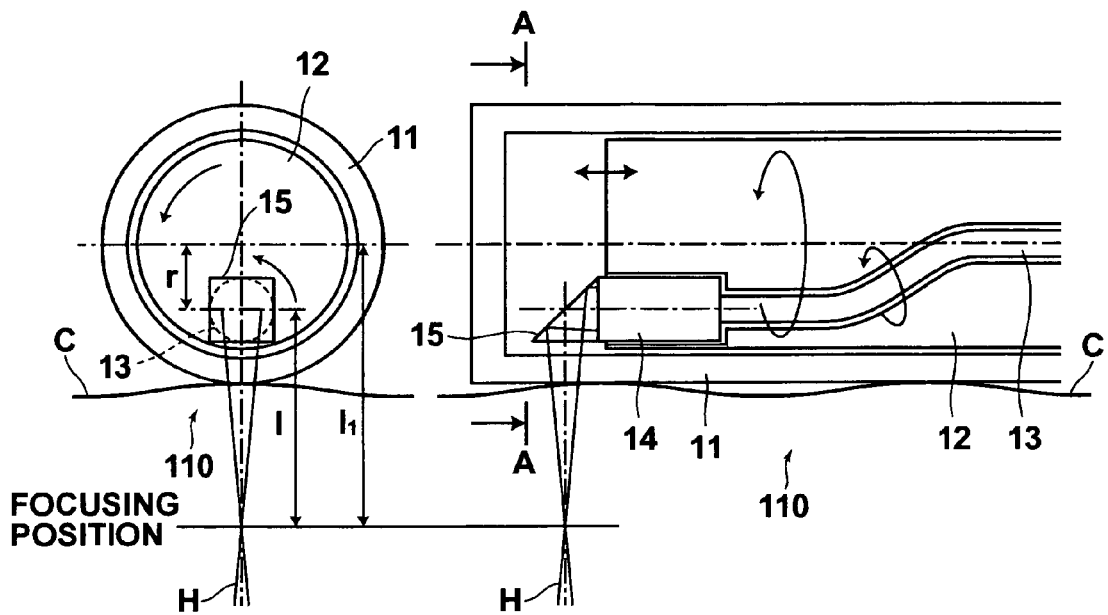

FIG. 21B is a side cross-sectional view of an optical probe 110 in accordance with a tenth embodiment of the present invention, and FIG. 21A is a front cross-sectional view of the optical probe 110 taken along line A-A in FIG. 21B. For example, also the optical probe 110 forms a leading end portion of an endoscope which forms a part of an optical tomography system.

The optical probe 110 comprises a cylindrical sheath 11 which is closed at its leading end and is formed by transparent material, and a flexible shaft 12 which is disposed inside the cylindrical sheath 11. An optical fiber 13 which guides light from an interferometer (not shown) is passed through the flexible shaft 12, and GRIN lens (refractive index profile lens) 14 and a reflecting mirror 15 are disposed in the leading end portion of the flexible shaft 12. The optical fiber 13, the GRIN lens 14 and the reflecting mirror 15 are integrated and a portion from the leading end of the optical fiber to the reflecting mirror 15 is disposed in a position deviated from the axis of rotation of the flexible shaft 12 by r and is rotatable inside the flexible shaft 12.

The flexible shaft 12 is linearly movable inside the sheath 11 in the longitudinal direction of the sheath 11, that is, right and left in FIG. 21B, and is rotatable about the central axis of the sheath 11. The flexible shaft 12 is linearly moved and is rotated by a mechanism to be described later. Further, also the optical fiber 13 is rotated inside the flexible shaft 12 by the mechanism.

Figure 22:
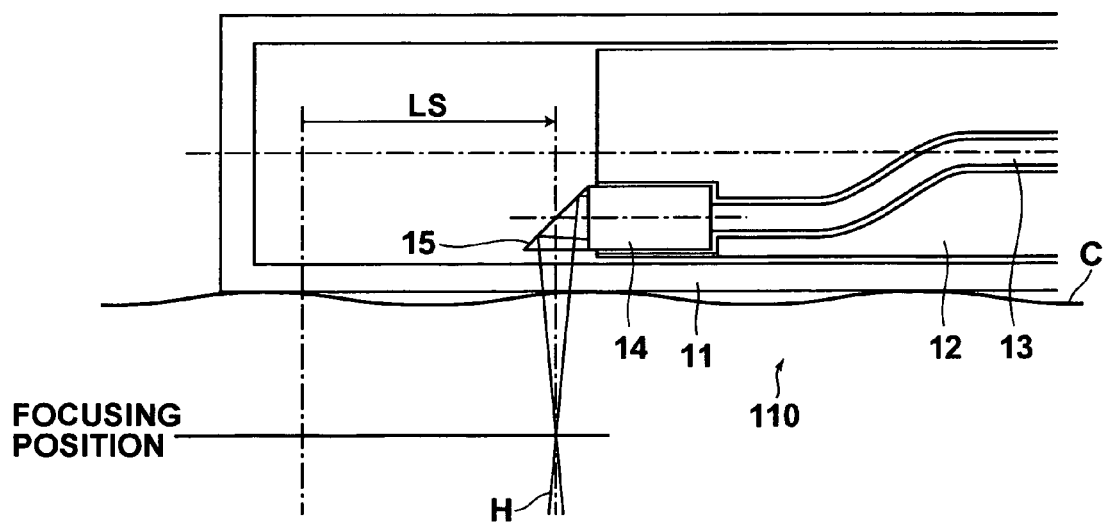
FIG. 22 is a side-cross sectional view showing the linear scanning by the optical probe shown in FIGS. 21A and 21B, FIGS. 23A and 23B are respectively a front cross-sectional view and a side cross-sectional view showing another state of the optical probe shown in FIG. 21.

Light beam H propagated through the optical fiber 13 is collected by the GRIN lens 14 and changes its direction of travel at the reflecting mirror 15 by 90°, thereby being converged on an outer portion of the circumference of the sheath 11. When the flexible shaft 12 is moved in the sheath 11 inside thereof, the light beam H radiated outward of the circumference of the sheath 11 is moved in this direction, whereby when the object is on the outer side of the sheath 11, the light beam H linearly scans the object in the longitudinal direction of the sheath 11. FIG. 22 shows a state where the flexible shaft 12 is moved from the state shown in FIGS. 21A and 21B by a distance LS.

When it is assumed in this structure that the distance from the reflecting mirror 15 to the focusing position of the GRIN lens 14 is 1, the distance $l_1$ from the central axis of the flexible shaft 12 to the focusing position of the GRIN lens 14 is expressed by the following formula (21) in the setup shown in FIGS. 21A and 21B.

$$l_1 = l + r \quad (21)$$

Figure 23:
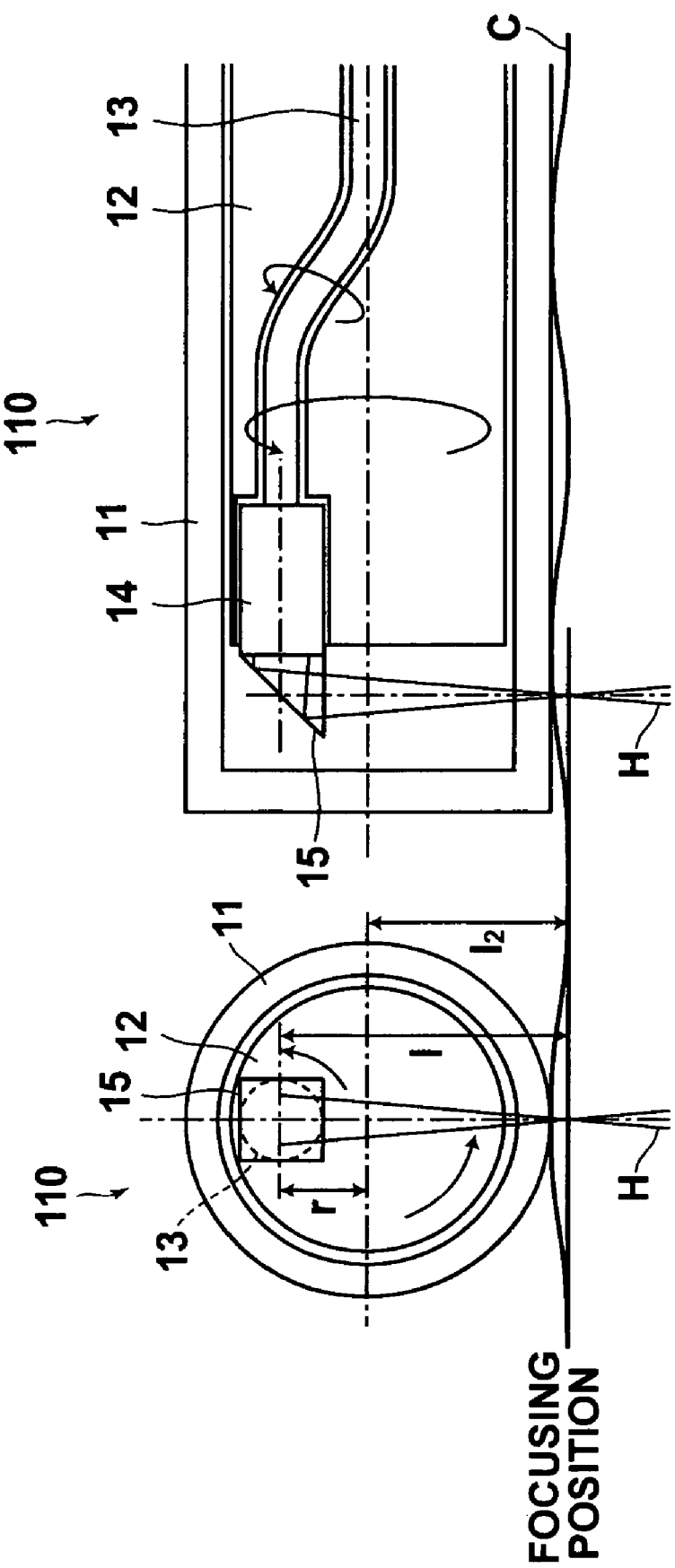

Whereas, FIGS. 23A and 23B show a state where the optical fiber 13 is rotated by 180° in the flexible shaft 12 to make reverse the direction of the reflecting mirror 15 relatively to the flexible shaft 12 and at the same time the flexible shaft 12 is rotated by 180° in the sheath 11. The distance from the central axis of the flexible shaft 12 to the focusing position at this time is expressed by the following formula (22).

$$l_2 = l - r \quad (22)$$

That is, the distance from the central axis of the flexible shaft 12 to the focusing position of the light beam H can be freely changed between the maximum $l_1$ and the minimum $l_2$. The width of the change is expressed by the following formula (23).

$$l_1 - l_2 = 2r \quad (23)$$

When the outer diameter of the sheath 11 is R, the depth of the focusing position from the outer periphery of the sheath is $l_1 - R$ at the largest and $l_2 - R$ at the smallest. This is the actual range of the depth of the focusing position in the object C. However, in order to continuously change the focusing position in the vertical direction of FIGS. 21 to 23, the projecting direction of the light beam H must be set obliquely in the cross-section perpendicular to the longitudinal direction, that is, at an angle to the direction of depth (for instance, a state shown in FIG. 3) other than the state where the focusing position takes the maximum depth $l_1 - R$ or the minimum depth $l_2 - R$. Accordingly, it is necessary to set the angular positions of the optical fiber 13 and the flexible shaft 12 according to the projecting direction of the light beam H to be set.

When an optical tomography system is formed by the optical probe 110 of this embodiment where the focusing position of the light beam H can be linearly changed in the direction of depth of the object C (in the direction of depth of focus) as described above, and the light beam H can be linearly scanned in the longitudinal direction of the sheath 11, a tomographic image of a two-dimensional cross-section including the direction of depth of the object C and the direction of the axis of the flexible shaft 12 can be obtained.

The projecting direction of the light beam H may be constantly a direction of depth of the projection without being oblique. In this case, it is necessary to provide a mechanism for laterally (right and left in FIG. 21A) moving the sheath 11 and to control the movement thereof in synchronization with rotation of the optical fiber 13 and the flexible shaft 12. For example, when the flexible shaft 12 is clockwisely rotated by 90° and the optical fiber is counterclockwisely rotated by 90° from the state of FIG. 21A, the sheath 11 may be moved rightward in FIG. 21A by r.

Figure 24:
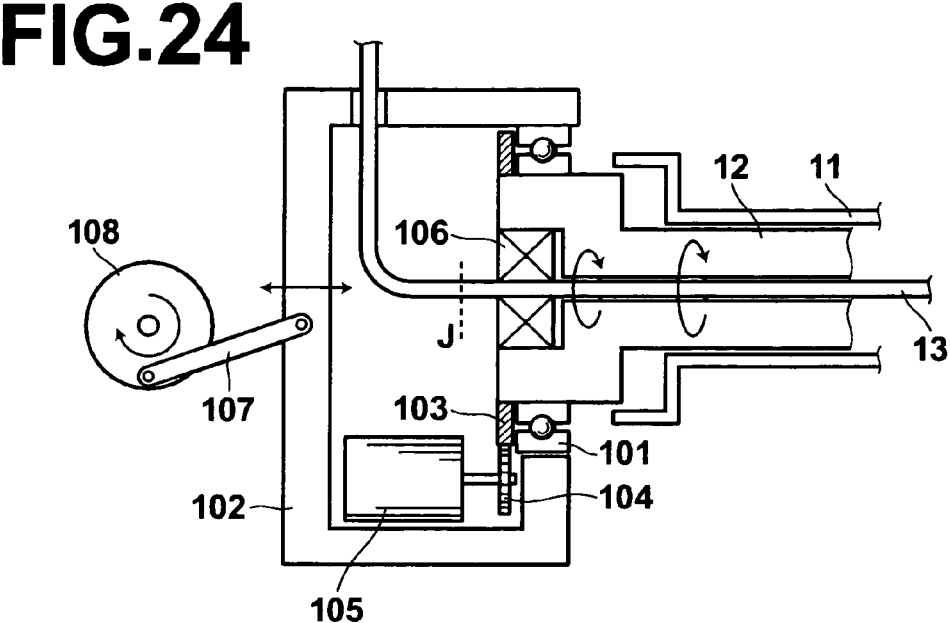
FIG. 24 is a side cross-sectional view showing another part of the optical probe shown in FIGS. 21A and 21B, FIGS. 25A and 25B are respectively a front cross-sectional view and a side cross-sectional view of an optical probe in accordance with a eleventh embodiment of the present invention.

A mechanism for linear movement and rotation of the flexible shaft 12 and for rotation of the optical fiber 13 will be described with reference FIG. 24, hereinbelow. FIG. 24 shows a base portion of the sheath 11 and the flexible shaft 12 and the vicinity thereof opposite to the leading end portion thereof. As shown in FIG. 24, the flexible shaft 12 is supported for rotation by a probe receiving portion 102 by way of a shaft bearing 101. The base portion of the flexible shaft 12 is in mesh with a spur gear 103 and another spur gear 104 is in mesh with the spur gear 103. The spur gear 104 is rotated by a shaft rotating motor 105, whereby the flexible shaft 12 is rotated inside the sheath 11.

A fiber rotating motor 106 is disposed in the base portion of the flexible shaft 12 and optical fiber 13 is rotated in the flexible shaft 12 relatively thereto as described above by rotation of the motor 106.

An end of a rod 107 is connected to the probe receiving portion 102 and the other end of the rod 107 is connected to the vicinity of the periphery of a rotary disk 108. The rod 107 and the disk 108 form a slider-crank mechanism. Accordingly, when the disk 108 is rotated by a driving means (not shown), the probe receiving portion 102 is moved right and left in FIG. 24 and the flexible shaft 12 is linearly moved in the longitudinal direction of the sheath 11 inside thereof. The flexible shaft 12 may be linearly moved, for instance, by an electromagnetic actuator instead of the slider-crank mechanism.

In this embodiment, since the flexible shaft 12 is rotatable in the sheath 11, it is possible to rotatively scan the light beam H in response to rotation of the flexible shaft 12 as in the optical probe 10 of the first embodiment. In this case, since not only a tomographic image in the longitudinal direction of the sheath 11 but also a tomographic image in the circumferential direction of the sheath 11 can be obtained, a three-dimensional tomographic image can be formed.

When the light beam H is only linearly scanned without rotary scan thereof, the rotating range of the optical fiber 13 may only have to be ensured by 360°. It is preferred that though the direction of the optical fiber 13 is changed by 90° in the probe receiving portion 102, twist is absorbed in response to rotation by 360° (described above) at most by providing a play in the part where the direction of the optical fiber 13 is changed. When it is difficult to do so, a coupling means may be disposed in the vicinity of the part where a twist is generated, that is, a part shown by the broken line J in FIG. 24 so that the two parts of the optical fiber 13 are coupled together there. However, since a light propagation loss is generated in the coupling and/or the coupling can add to the cost in this case, it is preferred that the optical fiber 13 comprises a single part.

Though the optical tomography system on the basis of measurement of OCT, especially FD-OCT (Fourier domain OCT), is generally able to scan the direction of depth at high speed, the tomographic image obtaining range thereof is limited to a region close to a focusing position. When a high resolution is required, it is necessary to increase the NA, thereby improving the lateral resolution. However, as the NA increases, the depth of focus becomes shallower and the resolution is rapidly deteriorated when deviated from the focusing position. Accordingly, a mechanism for changing the focusing position, that is, a dynamic focus mechanism, is necessary to ensure a high resolution over a wider range in the direction of depth. The optical probe 110 of this embodiment satisfies the requirement.

An optical probe 120 in accordance with an eleventh embodiment of the present invention will be described with reference to FIGS. 25A, 25B, 26A and 26B, hereinbelow. The relation between A and B in these drawings is the same as that between FIGS. 21A and 21B. The optical probe 120 of this embodiment differs from the optical probe 110 shown in FIGS. 21A to 23B only in that the NA changing lens 21 is provided.

That is, in the optical probe 120, the NA changing lens 21 is fixed to the leading end of the flexible shaft 12. The NA changing lens 21 is disposed opposite to the reflecting mirror 15 with the central axis of the flexible shaft 12 interposed therebetween.

Figure 25A:
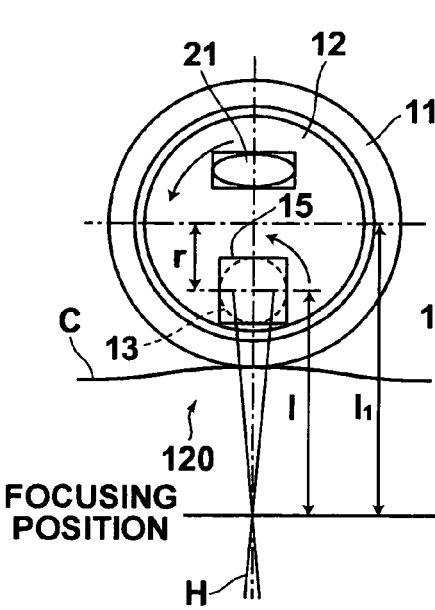
Figure 25B:
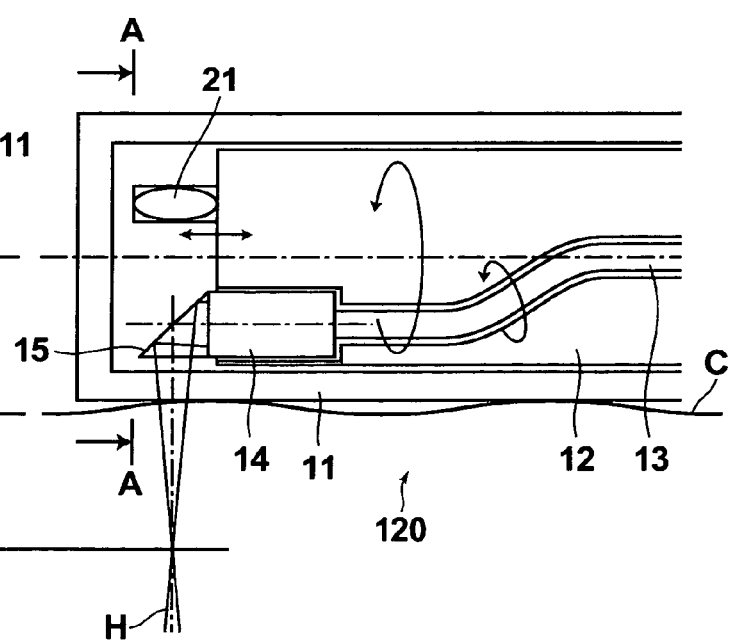

In a state shown in FIGS. 25A and 25B where the distance from the central axis of the flexible shaft 12 to the focusing position of the light beam H is maximized to $l_1$, light beam H radiated from the reflecting mirror 15 travels in the direction opposite to the NA changing lens 21 and does not pass through the NA changing lens 21. Whereas, in a state shown in FIGS. 26A and 26B where the distance from the central axis of the flexible shaft 12 to the focusing position of the light beam H is minimized to $l_2$, light beam H radiated from the reflecting mirror 15 travels toward the NA changing lens 21 and passes through the NA changing lens 21.

In the case where the NA changing lens 21 is a convex lens, the NA to the light beam H is increased from the case when the light beam H does not pass through the NA changing lens 21, and the lateral resolution in the focusing position is improved. Conversely, in the case where the NA changing lens 21 is a concave lens, the NA to the light beam H is decreased from the case when the light beam H does not pass through the NA changing lens 21, and the lateral resolution in the focusing position is deteriorated. As the NA increases, though being better in the focusing position, the lateral resolution is rapidly deteriorated when deviated from the focusing position in the direction of the optical axis (direction of depth of the object). By employing the arrangement of this embodiment, the NA can be reduced when the measurement is to be done over a range wide in the direction of depth, the NA can be increased when the measurement is to be done at a high resolution only at the aimed depth.

Though, in the optical probe 120 in accordance with this embodiment, a state where light beam H is passed through the NA changing lens and a state where light beam H is not passed through the NA changing lens can be selectively set, even in the optical probe where the light beam H is linearly scanned, the arrangement in FIG. 12 may be employed so that the light beam H is passed through one of a plurality of the NA changing lenses different from each other.

What is claimed is:

1. An optical probe comprising
   a tubular outer envelope,
   a shaft which is rotatable about an axis of rotation extending longitudinal direction of the outer envelope inside the outer envelope,
   a light guide means which is disposed inside the outer probe to extend along the shaft and is connected to the shaft at least at its leading end portion,
   a light deflecting means which is connected to the leading end portion of the light guide means and deflects light radiated from the leading end portion of the light guide means, and
   a collecting lens which converges light radiated from the light deflecting means outside the outer envelope,
   wherein the improvement comprises that light emitted from the light deflecting means is rotatively scanned in the direction of circumference of the outer envelope in response to rotation of the shaft and the light deflecting means is connected to the shaft in a position deviated from the axis of rotation of the shaft and is movable relatively to the shaft so that the direction of light deflected by the light deflecting means can be changed in this position.

2. An optical probe as defined in claim 1 in which an optical fiber is employed as the light guide means and the optical fiber connected to the shaft at its leading end portion is movable relatively to the shaft by rotation of the optical fiber about its axis.

* * * * *